(12) United States Patent
Lin et al.

(10) Patent No.: US 7,151,179 B2
(45) Date of Patent: Dec. 19, 2006

(54) PROCESS FOR THE PREPARATION OF 7-ALKYL-10-HYDROXY-20(S)-CAMPTOTHECIN

(75) Inventors: Chien-Hsing Lin, Taipei County (TW); Yung-Fa Chen, Tainan County (TW); Kau-Ming Chen, Tainan County (TW)

(73) Assignee: Scinopharm Taiwan, Ltd., Tainan County (TW)

( * ) Notice: Subject to any disclaimer, the term of this patent is extended or adjusted under 35 U.S.C. 154(b) by 327 days.

(21) Appl. No.: 10/844,225

(22) Filed: May 12, 2004

(65) Prior Publication Data

US 2004/0235878 A1 Nov. 25, 2004

Related U.S. Application Data

(60) Provisional application No. 60/469,737, filed on May 12, 2003.

(51) Int. Cl.
*C07D 405/14* (2006.01)

(52) U.S. Cl. ........................................ 546/48

(58) Field of Classification Search ................... 546/48
See application file for complete search history.

(56) References Cited

U.S. PATENT DOCUMENTS 5,734,056 A 3/1998 Burk et al.

OTHER PUBLICATIONS

Sawada et al, Chemical and Pharmaceutical Bulletin, 39(12), pp. 3183-3188 (1991).*

* cited by examiner

*Primary Examiner*—Bernard Dentz
(74) *Attorney, Agent, or Firm*—Cohen, Pontani, Lieberman & Pavane

(57) ABSTRACT

The key intermediate in any synthesis of Irinotecan is 7-ethyl-10-hydroxy-20(S)-camptothecin. A process for the efficient synthesis of this intermediate is demonstrated proceeding through readily available 20(S)-camptothecin. Various other tecan compounds may be made by use of corresponding 7-alkyl-10-hydroxy-20(S)-camptothecin intermediates.

16 Claims, No Drawings

PROCESS FOR THE PREPARATION OF 7-ALKYL-10-HYDROXY-20(S)-CAMPTOTHECIN

RELATED APPLICATIONS

This application claims priority from U.S. Provisional Patent Application Ser. No. 60/469,737 which was filed on May 12, 2003.

BACKGROUND OF THE INVENTION

1. Field of the Invention

This invention relates to an efficient three-step process for the preparation of 7-alkyl-10-hydroxy-20(S)-camptothecin from the readily available natural product, 20(S)-camptothecin. The invention also demonstrates a novel intermediate useful in this synthesis.

2. Description of the Related Art

Camptothecin derivatives have shown significant cytotoxic activity and several have been developed into useful pharmaceuticals. Specifically Irinotecan (Campto) has shown excellent activity toward colon-rectal cancers and is widely marketed. It shows considerable advantage over other camptothecin derivatives in that it is water soluble.

Irinotecan is prepared in several steps from the key intermediate, 7-ethyl-10-hydroxy-20(S)-camptothecin. Considerable effort has been expended to introduce both the 10-hydroxy and the 7-ethyl functionality into the camptothecin molecule. Therefore, while there is some prior art associated with each of these individual groups, there is very little knowledge on introduction of both these functionality simultaneously into the molecule.

Sawada (Chem. Pharma. Bull., 39(12), 3183(1991) demonstrates the synthesis of 7-ethyl-10-hydroxy-20(S)-camptothecin through the synthesis of 7-ethyl-20(S)-camptothecin by known means, the subsequent formation of an N-oxide and the photochemical rearrangement to provide 7-ethyl-10-hydroxy-20(S)-camptothecin. However, this synthesis suffers considerably from the insolubility of 7-ethyl-20(S)-camptothecin in suitable solvents and thus only small quantities can be prepared.

10-Hydroxy-20(S)-camptothecin has been prepared by the hydrogenation of 20(S)-camptothecin to 1,2,6,7-tetrahydro-20(S)-camptothecin and subsequent oxidation. Thus U.S. Pat. No. 5,734,056 describes the preparation through the hydrogenation of 20(S)-camptothecin to 1,2,6,7-tetrahydro-20(S)-camptothecin followed by the oxidation with iodosobenzene derivatives specifically esters such as iodobenzenediacetate. Japanese pat. No. 59-5188 discloses the hydrogenation of camptothecin followed by oxidation with agents such as CAN(cerium (IV) ammonium nitrate, chromic acid, potassium permanganate, Fremy's salt. Similarly, Sawada, et. al. (Chem. Pharm. Bull. 39(120)3183, 1991) describes a reduction and oxidation with lead tetraacetate. In all these cases, the use of a 7-substituted derivative has not been demonstrated.

The preparation of 7-ethyl-20(S)-camptothecin has been demonstrated previously through the Fenton reaction by employing 20(S)-camptothecin and propionaldehyde with ferrous sulfate and sulfuric acid.

Therefore there is a need for an efficient synthesis of 7-ethyl-10-hydroxy-20(S)-camptothecin which can be used in commercial scale.

SUMMARY OF THE INVENTION

The present invention provides as one embodiment a novel process employing the formation of the 7-ethyl-20(S)-camptothecin followed by the catalytic reduction and subsequent oxidation to the desired 7-ethyl-10-hydroxy-20(S)-camptothecin, shown in Scheme I, which is useful in the synthesis of Irinotecan.

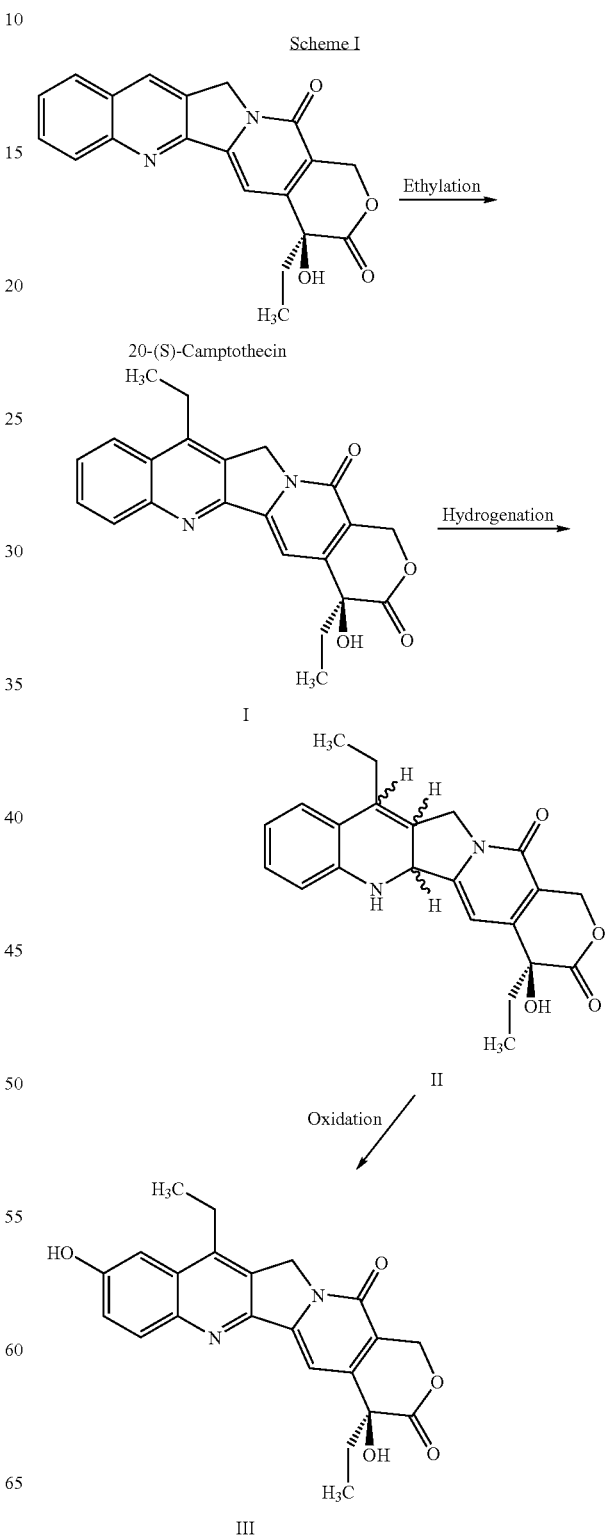

DETAILED DESCRIPTION OF THE INVENTION

The formation of 7-alkyl-20(S)-camptothecin (I) was accomplished by known methodology. It is known in the literature that the hydrogenation of tetra-substituted olefins is very difficult. Therefore, it was expected that the hydrogenation of this compound to 7-alkyl-1,2,6,7-tetrahydro-20 (S)-camptothecin (II) would be challenging. We were surprised to learn that we could indeed accomplish this hydrogenation in good yield and good purity using $PtO_2$ as the catalyst in a suitable solvent in which the 7-alkyl-20(S)-camptothecin is soluble. Catalysts other than $PtO_2$ may be used, such as reduction catalyst containing at least one of the elements platinum, rhodium, lawrencium, and ruthenium. Further, the hydrogenation step may be conducted with a catalysis modifier, such as dimethylsulfoxide and ammonium hydroxide. Acetic acid is a preferred solvent for this purpose. Other solvent systems such as alcohols and mixtures of acetic acid and alcohols can be employed in this hydrogenation but high solubility of camptothecin in acetic acid makes acetic acid the most desirable solvent. By employing this catalytic hydrogenation, the desired product can be easily obtained in greater than 90% yield.

It was found that unlike the known 1,2,6,7-tetrahydro-20 (S)-camptothecin, 7-alkyl-1,2,6,7-tetrahydro-20(S)-camptothecin (II) is oxidized readily back to 7-alkyl-20(S)-camptothecin (I) under an oxygen atmosphere. Therefore there was a question as to whether the oxidation would produce the 10-hydroxy derivative in good yield. In fact, the oxidation with iodobenzenediacetate in acetic acid/water did produce the desired 7-alkyl-10-hydroxy-20(S)-camptothecin (III) in very good yield. The reaction can be carried out in a variety of solvent systems but again acetic acid/water was the most convenient and preferred solvent system. Other suitable solvents include $C_1$–$C_6$ ester, $C_1$–$C_6$ acid, $C_1$–$C_6$ alcohol and water. More specifically, the $C_1$–$C_6$ acid may be butenic acid, propanoic acid and acetic acid. The reaction may also be carried out with various other oxidizing agents, including those containing hypervalent iodine, ruthenium (VIII), manganate (VII), osmium (VIII), lead (IV) and chromium (VI). The product precipitates during the reaction and can be collected by filtration. The product obtained is of sufficient purity to be used directly or it can be purified by recrystallization from organic solvents such as acetic acid.

Therefore the present invention provides for an efficient synthesis of 7-alkyl-10-hydroxy-20(S)-camptothecin (III).

EXAMPLES

Preparation of 7-ethyl-20(S)-camptothecin (I)

20(S)-camptothecin (60.0 g), ferrous sulfate heptahydrate (12.0 g) and 9N sulfuric acid (1200 ml) are subsequently charged to a 5-L reactor equipped with a mechanical stirrer, condenser and a thermometer under nitrogen atmosphere. The resulting mixture is stirred at 25° C. until all the suspension is dissolved, and it is cooled to between −10 and 0° C. Propionyl aldehyde (10.0 g) is added to the cold reaction mixture. A solution of 10% hydrogen peroxide (116.9 g) and propionyl aldehyde (15.0 g) are simultaneously charged to the cold reaction mixture over a period of 30–60 minutes, while maintaining the temperature at 10 to 0° C. The resulting mixture is stirred at the same temperature for 60 to 90 minutes. The reaction mixture was diluted with water and neutralized with aqueous ammonium hydroxide to precipitate out the desired product. The crude product was crystallized from acetic acid and water to give compound I, 49.83 g in 71.6% yield with purity of 95.16% by HPLC. 1H-NMR (DMSO-$d_6$) δ: 0.9 (3H, t), 1.3 (3H, t), 1.85 (2H, q), 3.2 (2H, q), 5.28 (2H, s), 5.44 (2H, s), 6.5 (1H, s), 7.32 (1H, s), 7.7 (1H, dd), 7.85 (1H, dd), 8.15 (1H, d), 8.26 (1H, d).

Preparation of 7-ethyl-1,2,6,7-tetrahydro-20(S)-camptothecin (II)

7-ethyl-20(S)-camptothecin (I) (30.0 g) and acetic acid (900 ml) were charged together and heated to 80° C. to facilitate the dissolution. The resulting solution is then transferred to a 2-L autoclave reactor and cooled to room temperature. Ammonium hydroxide (30% contents, 3.4 ml), platinum oxide and dimethyl sulfoxide (2.2 ml) were added into the resulting suspension at 25° C. The resulting mixture is then subjected to hydrogenation at a hydrogen pressure of 5 bars until the starting material, 7-ethyl-20(S)-camptothecin I, disappeared by TLC analysis. The catalyst was removed by filtering through a pad of celite and washed with acetic acid, the resulting solution is used directly for the next reaction. The sample was characterized by HPLC, NMR, IR and LC/MS analysis. HPLC shows three diastereoisomers in a ratio of 6: 61: 13, which are detected by LC/MS to have MS m/z: 380 ($M^{3o}$). 1H-NMR (DMSO-$d_6$) δ: 0.78 (3H, t), 0.82(3H, m), 1.2–1.35 (2H, m), 1.8 (3H, m), 2.65 (1H, m), 3.12 (1H, m), 3.75 (1H, dd), 4.08 (1H, dd), 4.92 (1H, dd), 5.23 (1H, s), 6.48 (1H, s), 6.5–6.98 (4H, m), 6.62 (1H, s); IR (KBr) v: 3310, 2967, 1744, 1652, 1586, 1491, 1465 $cm^{-1}$.

Preparation of 7-ethyl-10-hydroxy-20(S)-camptothecin (III)

The hydrogenated filtrate of 7-ethyl-1,2,6,7-tetrahydro-20 (S)-camptothecin was charged to a 3-L, four-necked round bottom flask equipped with a mechanical stirrer, thermometer under nitrogen atmosphere, and was cooled to 10° C. Water (900 ml) was added to the solution and the resulting solution was stirred at this temperature for 20 minutes. Subsequently, iodobenzene diacetate (65.5 g) was added to the solution in several small portions, while maintaining the temperature below 10° C. The resulting mixture was stirred at this temperature until the complete disappearance of the starting material, 7-ethyl-1,2,6,7-tetrahydro-20(S)-camptothecin (II), as monitored by TLC. The reaction was quenched by the addition of Methanol (230 ml) to facilitate the precipitation of the product. The reaction slurry was then filtered and the collected solids are washed with aqueous acetic acid and methanol to give the desired product 28.3 g (90% overall yield in two steps). 1H-NMR (DMSO-$d_6$) δ: 0.9 (3H, t), 1.32 (3H, t), 1.88 (2H, q), 3.1 (2H, q), 5.28 (1H, s), 5.42 (1H, s), 6.46 (1H, s), 7.28 (1H, s), 7.4 (2H, m), 8.0 (1H, d), 10.5 (1H, s).

Preparation of 7-methyl-20(S)-camptothecin

We performed a process corresponding to the above process to make 7-ethyl-20(S)-camptothecin to provide the product, 25.6 g in 60% yield. 1H-NMR (DMSO-$d_6$) δ: 0.90 (3H, t), 1.88 (2H, m), 2.79 (3H, s), 5.29 (2H, s), 5.44 (2H, s), 6.51 (1H, s), 7.34 (1H, s), 7.73 (1H, t), 7.86 (1H, t), 8.15 (1H, d), 8.25 (1 H, d).

Preparation of 7-methyl-1,2,6,7-tetrahydro-20(S)-camptothecin

We performed a process corresponding to the above process to make 7-ethyl-1,2,6,7-tetrahydro-20(S)-camptothecin. HPLC of the product shows three diastereoisomers in a ratio of 13: 68: 19, 1H-NMR (DMSO-$d_6$) δ: 0.78 (3H, t), 1.02 (3H, d), 1.72 (2H, m), 1.90 (3H, m), 3.01 (1H, m), 3.17 (1H, m),3.91 (1 H, m), 4.06(1H, m), 4.91 (1H, m), 5.21 (1H, s), 6.30 (1H, s), 6.56–6.6 (2H, m), 6.8–7.0 (2H, m).

Preparation of 7-methyl-10-hydroxy-20(s)-camptothecin

We performed a process corresponding to the above process to make 7-ethyl-10-hydroxy-20(s)-camptothecin (III). The HPLC of the reaction product shows 17% of the desired product and 41% 7-methyl-20(S)-camptothecin.

References that are cited herein are incorporated by reference in their entirety.

Thus, while there have shown and described and pointed out fundamental novel features of the invention as applied to a preferred embodiment thereof, it will be understood that various omissions and substitutions and changes in the form and details of the process illustrated, and in its operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A compound of the formula:

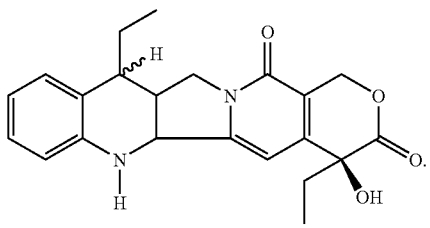

2. A process for the preparation of 7-ethyl-10-hydroxy-20(S)-camptothecin of formula:

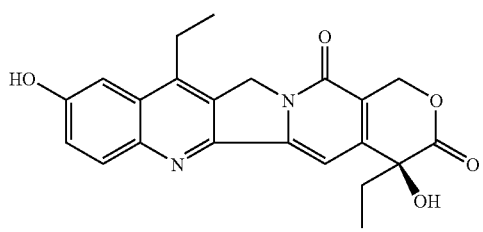

comprising the steps of:
reducing 7-ethyl-20(S)-camptothecin to 7-ethyl-1,2,6,7-tetrahydro-20(S)-camptothecin with hydrogen gas catalyzed by a reduction catalyst; and
oxidizing the 7-ethyl-1,2,6,7-tetrahydro-20(S)-camptothecin with an oxidizing agent to produce 7-ethyl-10-hydroxy-20(S)-camptothecin.

3. The process of claim 2, wherein the oxidizing agent is selected from the group consisting of hypervalent iodine, ruthenium (VIII), manganate (VII), osmium (VIII), lead (IV) and chromium (VI).

4. The process of claim 2, wherein the oxidizing agent is iodobenzenediacetate.

5. The process of claim 2, wherein the oxidizing step is performed in a solvent system.

6. The process of claim 2 wherein the organic solvent is selected from the group consisting of $C_1$–$C_6$ ester, $C_1$–$C_6$ acid, $C_1$–$C_6$ alcohol and water.

7. The process of claim 6 wherein the $C_1$–$C_6$ acid is selected from the group consisting of butenic acid, propanoic acid, and acetic acid.

8. The process of claim 6 wherein the $C_1$–$C_6$ acid is acetic acid.

9. The process of claim 2, wherein the reduction catalyst comprises the element selected from the group consisting of platinum, rhodium, lawrencium, and ruthenium.

10. The process of claim 2, wherein the reducing step is performed in the presence of a catalysis modifier.

11. The process of claim 10 wherein the catalyst modifier is dimethylsulfoxide.

12. The process of claim 10 wherein the catalyst modifier is ammonium hydroxide.

13. A process of producing irinotecan comprising:
reducing 7-ethyl-20(S)-camptothecin to 7-ethyl-1,2,6,7-tetrahydro-20(S)-camptothecin with hydrogen gas catalyzed by a reduction catalyst;
oxidizing the 7-ethyl-1,2,6,7-tetrahydro-20(S)-camptothecin with an oxidizing agent to produce 7-ethyl-10-hydroxy-20(S)-camptothecin; and
using 7-ethyl-10-hydroxy-20(S)-camptothecin as an intermediate to prepare the irinotecan product.

14. A compound of the formula:

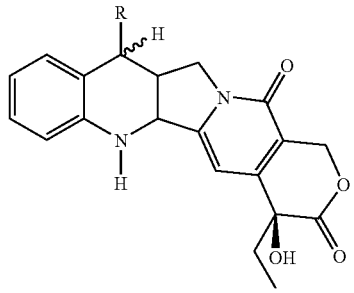

wherein R is a lower alkyl group having 1 to 6 carbon atoms.

15. A process for the preparation of 7-alkyl-10-hydroxy-20(S)-camptothecin of the formula

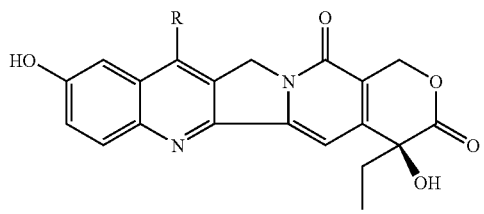

wherein R is an alkyl group, comprising the steps of:
reducing 7-alkyl-20(S)-camptothecin to 7-alkyl-1,2,6,7-tetrahydro-20(S)-camptothecin with hydrogen gas catalyzed by a reduction catalyst; and
oxidizing the 7-alkyl-1,2,6,7-tetrahydro-20(s)-camptothecin with an oxidiong agent to produce 7-alkyl-10-hydroxy-20(S)-camptothecin.

16. A process for producing tecans comprising the process according to claim 15.

* * * * *